United States Patent
Ayre et al.

(10) Patent No.: US 7,859,208 B2
(45) Date of Patent: Dec. 28, 2010

(54) TUNING DC BRUSHLESS MOTORS

(75) Inventors: Peter Joseph Ayre, Crows Nest (AU);
Lee Thomas Glanzmann, Darlinton (AU); Nicholas Oliver Von Huben, Bexley North (AU)

(73) Assignee: Thoratec Corporation, Pleasanton, CA (US)

( * ) Notice: Subject to any disclaimer, the term of this patent is extended or adjusted under 35 U.S.C. 154(b) by 200 days.

(21) Appl. No.: 12/097,879

(22) PCT Filed: Dec. 18, 2006

(86) PCT No.: PCT/AU2006/001921
§ 371 (c)(1),
(2), (4) Date: Jun. 17, 2008

(87) PCT Pub. No.: WO2007/070932
PCT Pub. Date: Jun. 28, 2007

(65) Prior Publication Data
US 2008/0258657 A1  Oct. 23, 2008

(30) Foreign Application Priority Data
Dec. 19, 2005  (AU) .............................. 2005907151

(51) Int. Cl.
*H03K 5/00* (2006.01)
(52) U.S. Cl. .................. 318/400.13; 318/400.34; 318/400.17; 318/432; 318/434
(58) Field of Classification Search .......... 318/400.13, 318/400.34, 400.17, 432, 434
See application file for complete search history.

(56) References Cited

U.S. PATENT DOCUMENTS

| | | | |
|---|---|---|---|
| 4,173,796 A | 11/1979 | Jarvik | |
| 4,928,043 A | 5/1990 | Plunckett | |
| 5,220,259 A * | 6/1993 | Werner et al. | 318/432 |
| 5,289,821 A | 3/1994 | Swartz | |
| 5,751,125 A | 5/1998 | Weiss | |
| 5,936,365 A | 8/1999 | Li et al. | |
| 6,027,498 A | 2/2000 | Mutch et al. | |
| 6,066,086 A | 5/2000 | Antaki et al. | |
| 6,071,093 A | 6/2000 | Hart | |
| 6,277,078 B1 | 8/2001 | Porat et al. | |
| 6,623,420 B2 | 9/2003 | Reich et al. | |
| 6,991,595 B2 | 1/2006 | Burke et al. | |
| 7,138,776 B1 | 11/2006 | Gauthier et al. | |
| 7,141,943 B2 * | 11/2006 | Song et al. | 318/400.34 |
| 7,645,225 B2 | 1/2010 | Medvedev et al. | |
| 2001/0009645 A1 | 7/2001 | Noda | |
| 2002/0183628 A1 | 12/2002 | Reich et al. | |
| 2003/0234623 A1 | 12/2003 | Douglas | |

FOREIGN PATENT DOCUMENTS

| | | |
|---|---|---|
| EP | 1246355 | 10/2002 |
| EP | 1 354 606 | 10/2003 |
| EP | 1482632 | 12/2004 |
| WO | WO 01/05023 | 1/2001 |

* cited by examiner

*Primary Examiner*—Walter Benson
*Assistant Examiner*—Erick Glass
(74) *Attorney, Agent, or Firm*—Squire, Sanders & Dempsey L.L.P.

(57) ABSTRACT

A method of tuning a DC brushless motor, wherein measurement of back EMF voltage is used to detect changes in the torque requirements caused by variation in the operating conditions of the DC brushless motor, the method including varying the timing of the driving signals to the motor to compensate for the changes in the torque requirements.

28 Claims, 5 Drawing Sheets

TUNING DC BRUSHLESS MOTORS

CROSS REFERENCE TO RELATED APPLICATIONS

This application is a National Stage of International Application No. Corresponds to PCT/AU2006/001921, filed Dec. 18, 2006.

FIELD OF THE INVENTION

The present invention relates to improvements to tuning DC brushless motors for optimal efficiency using back EMF detection. In particular, the invention relates to a method and a system for tuning DC brushless motors integrated in implantable blood pumps.

BACKGROUND OF THE INVENTION

DC Brushless motors (herein referred to as 'DCBM') have been used for a long time in a large range of general applications. Recently, DCBMs have increasingly been used in medical applications to drive small pumps. One such application includes the use of this type of motor in implantable medical devices including, but not limited to, blood pumps and drug infusers.

A DCBM usually comprises a rotor and a stator. The stator often includes three or more phases, wherein at least two of the phases are provided with driving signals to 15 facilitate the rotation of the rotor, while one phase is used to measure the back electromotive force (EMF). It is known in this field of art that the measured back EMF voltage may be used to detect the rotor position in the DC brushless motor. U.S. Pat. No. 4,928,043, to Plunckett et al., describes one example where the rotor position in a DC brushless motor is predicted and anticipated.

Usually the timing of the driving signals provided to the phases in the motor is predetermined with respect to the "typical" fluid dynamic conditions that the motor is expected to encounter. However, any deviation of the external environment from these "typical" conditions reduces the efficiency of the predetermined timing for sending the driving signals to the phases. This is of specific concern in the case of a DCBM being used in an implantable blood pump, if the back EMF control systems fail to correct for hematocrit changes and torque changes necessitated by varying blood temperature and viscosity. There may also be other load factors that can affect the efficiency of the DCBM that include, but are not limited to, the pulsatility of a natural heart. Accordingly, to improve the motor efficiency of DCBM, it is preferable if the motor is continuously tuned so that the firing sequence of the phases matches constantly the varying dynamics characteristics of the operating environment of the pump.

Previously, there have been two prior art methods of measuring back EMF. The first one conducts the EMF measurements based on the OFF periods of the pulse width modulation (PWM). In this case the generated back EMF signal passes from a negative voltage to a positive voltage and allows the so-called "zero crossing" technique to be applied. However, this method generally does not work wherein the PWM is at 100% since there is no OFF time.

The second method includes measuring of the back EMF during the ON periods of the PWM. The generated BEMF signal is always positive and, in theory, should cross halfway between the DC bus rail voltages. However, in practice, this often does not occur due to the circuitry and overall DCBM design. Furthermore, this method is generally not efficient across the whole operating spectrum (e.g. low-high speed, or low-high load).

The present invention aims to at least address or ameliorate one or more of the above problems.

SUMMARY OF THE INVENTION

According to one aspect of the invention, there is provided a method of tuning a DC brushless motor, wherein measurement of back EMF voltage is used to detect changes in the torque requirements caused by variation in the operating conditions of the DC brushless motor, the method including varying the timing of the driving signals to the motor to compensate for the changes in the torque requirements.

More preferably, the motor comprises a rotor and a stator, the stator including at least three phases, wherein alternating driving signals are provided simultaneously to at least two of the at least three phases such that, each switching cycle is a driving cycle, for at least two phases that receive driving signals during this cycle, and the same switching cycle is a listening cycle for at least one phase that is non-energised during this cycle, the motor being arranged such that, for a given switching cycle, a rotation of the rotor generates in the at least one listening phase a back EMF voltage that varies between two extreme values, the method including the steps of:

for at least one reference switching cycle:
  detecting the back EMF voltage from the at least one listening phase;
  determining the back EMF voltage corresponding to the midpoint value between the extreme values to define a reference voltage value; and
  calculating the time delay for the back EMF voltage to change from the midpoint value to the final extreme value to define a reference delay time;

then, for at least one further switching cycle, having a further at least one listening phase and a further set of at least two driving phases, the further cycle being subsequent to the reference cycle:
  monitoring the back EMF voltage in the further listening phase and, when the back EMF voltage reaches a value equal to the reference voltage value of the reference switching cycle; and
  providing a driving signal to the corresponding driving phases with a time delay with respect to the reference voltage point, which time delay is equal to the reference delay time.

Preferably, the method further includes comparing the back EMF voltages for two listening cycles of at least one phase and performing at least one of the following steps:

comparing the extreme values for both cycles and, if there is a difference between the corresponding extreme values, amending the reference delay time; and comparing the slopes of both graphs and, if the slopes are different, amending the voltage reference value with respect to the previously determined midpoint value and applying a time delay with respect to the amended reference voltage value.

More preferably, amending the reference delay time comprises:

if the extreme back EMF voltage values of the later cycle are smaller than the corresponding values of the earlier cycle, reducing the reference delay time for the following driving cycle; and if the extreme back EMF voltage values of the later cycle are bigger than the corresponding values of the earlier cycle, increasing the reference delay time for the following driving cycle.

Even more preferably, amending the reference voltage values comprises:

if the slope of the back EMF voltage of the later cycle is smaller than the slope of the back EMF voltage for the earlier cycle, increasing the reference voltage value for the following driving cycle; and if the slope of the back EMF voltage of the later cycle is larger than the slope of the back EMF voltage for the earlier cycle, reducing the reference voltage value for the following driving cycle.

Preferably, the switching cycle is adjacent to the reference cycle and/or the two compared listening cycles are adjacent.

Preferably, the tuning is effected either each switching cycle or each number of switching cycles.

More preferably, the motor is included in a fluid pump and the tuning is in response to variations in the fluid characteristics and/or fluid dynamics characteristics of the pumped fluid.

Even more preferably, the fluid pump is included in an implantable medical device and the fluid is human blood.

According to a second aspect of the invention, there is provided DC brushless motor system with varying characteristics of the input drive signals, wherein measurement of back EMF voltage is used to detect changes in the torque requirements caused by variation in the operating conditions of the motor, the system being configured to vary the timing of the drive signals to the motor to compensate for the changes in the torque requirements.

More preferably, the motor system comprises a rotor and a stator, the stator including at least three phases, wherein alternating driving signals are provided simultaneously to at least two of the at least three phases such that, each switching cycle is a driving cycle for at least two phases that receive driving signals during this switching cycle, and is a listening cycle for at least one listening phase that is non-energised during this cycle, the motor system being arranged such that, for a given switching cycle, a rotation of the rotor generates in the at least one listening phase a back EMF voltage that varies between two extreme values, the system further comprising:

a sensor for detecting the back EMF voltage from the listening phase;

processing means associated with the sensor and arranged for determining, during a reference switching cycle, a reference voltage value equal to the midpoint voltage value between the two corresponding extreme values and calculating a reference delay time equal to the delay time for the back EMF voltage to change from the midpoint value to the final extreme value; and control means for providing, during at least one cycle that is further to the reference cycle, driving signal to the corresponding driving phases with a delay, with respect to the reference voltage value, which is equal to the determined reference delay time.

Preferably, the processing means are further configured to compare the back EMF voltage graphs for two listening cycles of at least one phase and perform at least one of the following steps:

comparing the extreme values for both cycles and, if there is a difference between the corresponding extreme values, amending the reference delay time; and comparing the slopes of both graphs and, if the slopes are different, amending the voltage reference value with respect to the previously determined midpoint value and applying a time delay with respect to the amended reference voltage value.

Even more preferably, amending the reference delay time comprises:

if the extreme back EMF voltage values of the later cycle are smaller than the corresponding values of the earlier cycle, reducing the reference delay time for the following driving cycle; and if the extreme back EMF voltage values of the later cycle are bigger than the corresponding values of the earlier cycle, increasing the reference delay time for the following driving cycle.

Also more preferably, amending the reference voltage values comprises:

if the slope of the back EMF voltage of the later cycle is smaller than the slope of the back EMF voltage for the earlier cycle, increasing the reference voltage value for the following driving cycle; and if the slope of the back EMF voltage of the later cycle is larger than the slope of the back EMF voltage for the earlier cycle, reducing the reference voltage value for the following driving cycle.

Preferably, the switching cycle is adjacent to the reference cycle and/or the two compared listening cycles are adjacent.

More preferably, the tuning is effected either each switching cycle or each number of switching cycles.

Also preferably, the system is arranged for inclusion in a fluid pump, the tuning being required in response to variations in the fluid characteristics and/or fluid dynamics characteristics of the pumped fluid.

More preferably, the fluid pump is included in an implantable medical device, and the fluid is blood.

According to a third aspect of the invention, there is provided method of tuning a DC brushless motor integrated in a blood pump, wherein measurement of back EMF voltage is used to detect changes in the torque requirements caused by variation in the blood characteristics or blood dynamics characteristics, the method including varying the timing of the drive signals to the motor to compensate for the changes in the torque requirements, wherein the motor comprises a rotor and a stator, the stator including at least three phases, wherein alternating driving signals are provided simultaneously to at least two of the at least three phases such that, each switching cycle is a driving cycle, for at least two of the phases that receive driving signals, and the same switching signal is a listening cycle for at least one listening phase that is non-energised during this cycle the motor being arranged such that, for a given switching cycle, a rotation of the rotor generates in the at least one listening phase a back EMF voltage that varies between two extreme values, the method including the steps of:

for at least one reference switching cycle:

detecting the back EMF voltage from the at least one listening phase;

determining the back EMF voltage corresponding to the midpoint value between the extreme values to define a reference voltage value; and calculating the time delay for the back EMF voltage to change from the midpoint value to the final extreme value to define a reference delay time;

then, for at least one further switching cycle having a further at least one listening phase and a further set of at least two driving phases, the further cycle being subsequent to the reference cycle:

monitoring the back EMF voltage in the further listening phase and, when the EMF voltage reaches a value equal to the reference voltage value; and providing a driving signal to the corresponding driving phases with a time delay with respect to the reference voltage point, equal to the reference delay time.

Preferably, the method further includes comparing the back EMF voltage graphs for two adjacent listening cycles of a single phase and performing at least one of the following steps:

comparing the extreme values for both cycles and, if the extreme back EMF voltage values of the later cycle are smaller than the corresponding values of the earlier cycle, reducing the reference delay time for the following driving cycle; and if the extreme back EMF voltage values of the later cycle are bigger than the corresponding values of the earlier cycle, increasing the reference delay time for the following driving cycle; and comparing the slopes of both graphs and, if the slope of the back EMF voltage of the later cycle is smaller than the slope of the back EMF voltage for the earlier cycle, increasing the reference voltage value for the following driving cycle; and if the slope of the back EMF voltage of the later cycle is larger than the slope of the back EMF voltage for the earlier cycle, reducing the reference voltage value for the following driving cycle.

BRIEF DESCRIPTION OF THE DRAWINGS

Embodiments of the present invention will now be described with reference to the accompanying drawings wherein.

BEST MODE OF CARRYING OUT THE INVENTION

The preferred embodiment of the invention refers to a system and a method for tuning a DC brushless motor utilised within an implantable blood pump. Since the system and the method are closely associated, they will be described simultaneously in the following description.

Figure 1:
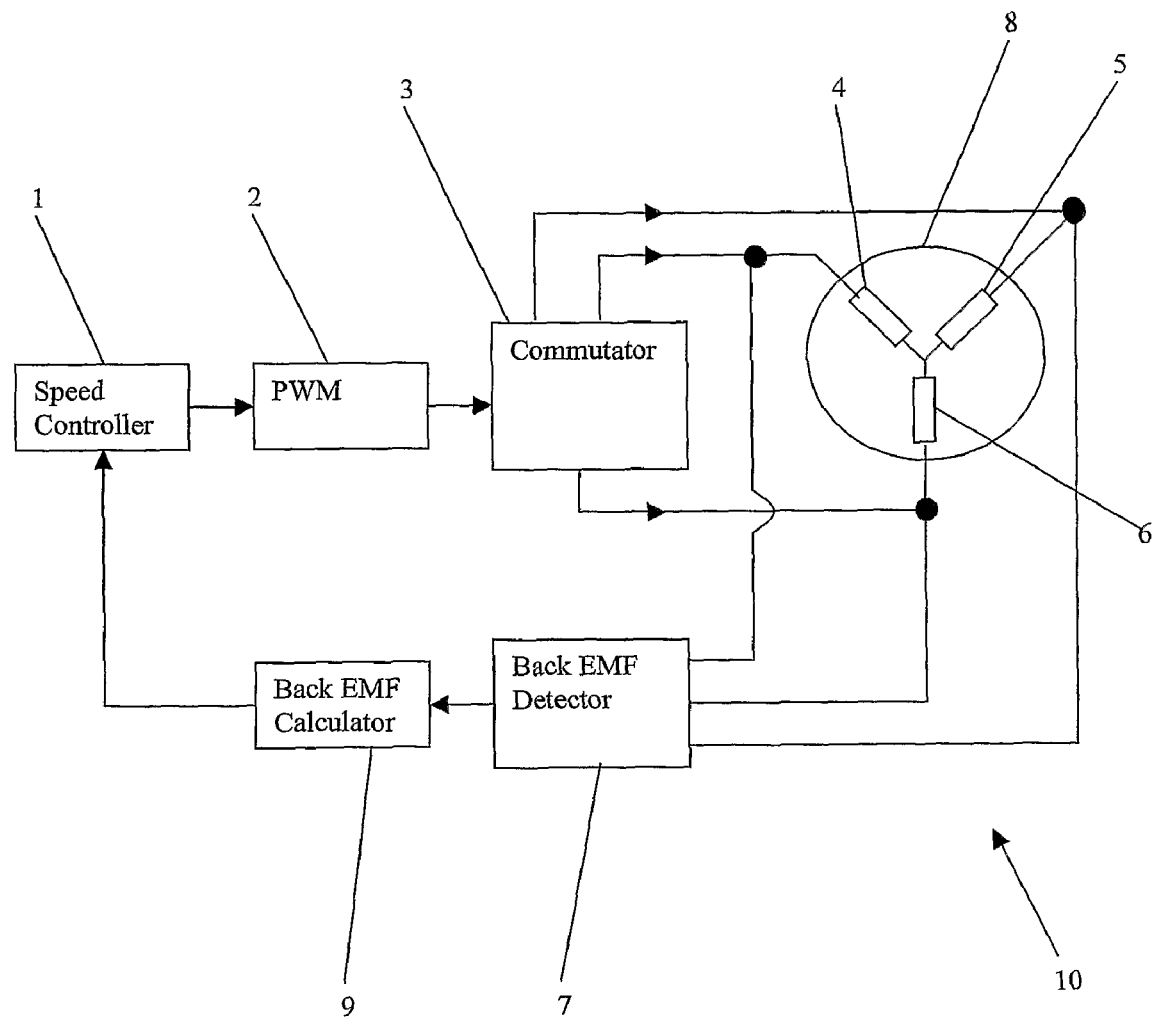
FIG. 1 depicts a schematic view of a DC brushless motor system according to the present invention.

In particular, the method and the system of the preferred embodiment are related to adjusting the timing of the drive signals provided to the stator phases in the DC brushless motor so as to compensate for changes in the torque requirements to the motor. Details of the system of the preferred embodiment of the invention are shown in FIG. 1. The DC brushless motor comprises three stationary phases 4, 5 and 6 and a rotating permanent magnet configuration 8. The location of magnet configuration 8 can vary with respect to phases 4 to 6. An important aspect is that, when driving signals are provided to the phases, the magnetic forces between the energised phases and the magnet configuration cause the rotation of the magnet configuration, thus driving the DC brushless motor. For this purpose, alternating driving signals are provided to phases 4, 5 and 6, such that each time when a driving signal is provided, to define a switching cycle, two phases receive driving signals, and are said to be in a "driving cycle" or to be "driving phases", and one phase does not receive driving signals and is said to be in a "listening cycle" or to be a "listening phase". The expression "listening phase" is used because the rotation of the rotor generates in this phase a back EMF voltage. This voltage can be detected and processed to obtain information of the position of the phase with respect to the permanent magnet configuration. Any shift of this position with time indicates a change in the torque requirements to the motor, which is usually caused by variation in the operating conditions of the DC brushless motor. One example of variation in the conditions is change in the temperature of the blood or change in the fluid dynamics of the blood caused by external factors.

Apart from the rotor/stator system 4, 5, 6 and 8, the system in FIG. 1 further includes a commutator 3, pulse width modulator 2 and a speed controller 1. The commutator 3 is a hardware device comprising an inverter bridge having a set of electronic switches that allow the system to switch each particular phase on and off. The driving signal provided by commutator 3 to the various phases is not a continuous voltage, but a train of square shaped pulses. The pulse width of this train of square pulses defines the energy introduced in the system and the rotational speed of the rotor. The pulse width modulator 2 is responsible for defining this pulse width and instructing commutator 3 appropriately. Ultimately, it is up to the speed controller 1 to define the driving characteristics of the rotor/stator system. In order to be able to optimise the operation of the brushless DC motor, speed controller 1 uses measurement of the back EMF generated in the listening phase of the corresponding switching cycle. These measurements are performed by detector 7 and are processed by calculator 9. Because this back EMF voltage is indicative of the position of the magnets with respect to phases 4, 5 and 6, the information for the generated back EMF is used to constantly adjust the driving parameters, when a deviation from the normal parameters is detected, thus improving the overall efficiency of the system.

Figure 2:
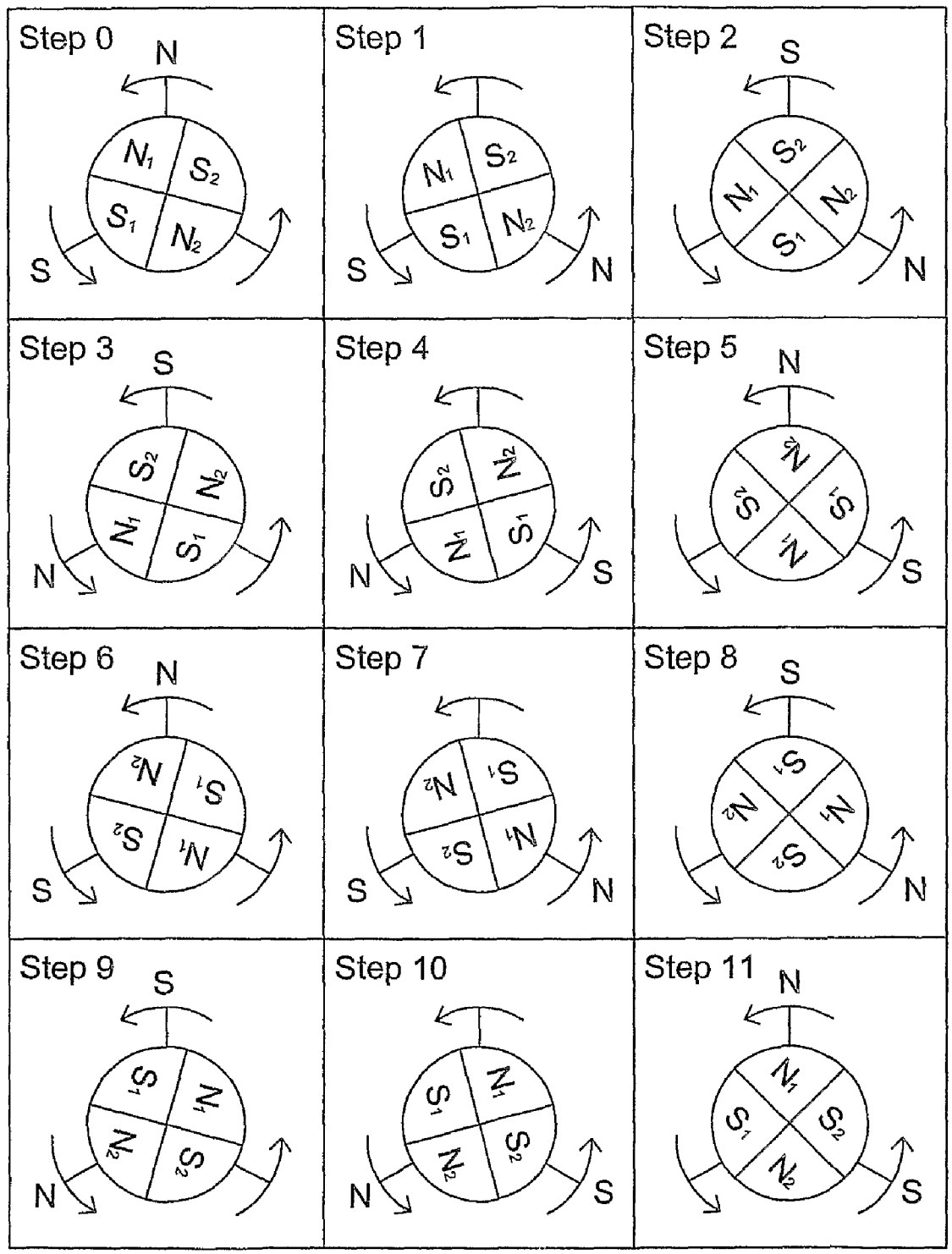
FIG. 2 depicts a schematic representation of various steps during the rotation of the rotor in the DC brushless motor of FIG. 1.

To explain the adjustments in more detail the varied rotational configurations positions of the rotor/stator system, represented in FIG. 2, will need to be considered. The magnetic polls of the permanent magnetic configuration are labelled with N1, S1 and N2, S2. The two energised phases in this particular driving cycle are represented with S and N. The third, non-labelled, phase does not receive driving signal during the particular switching cycle and is used to measure the back EMF voltage generated. Accordingly, this is the "listening" phase for this particular cycle.

Figure 4:
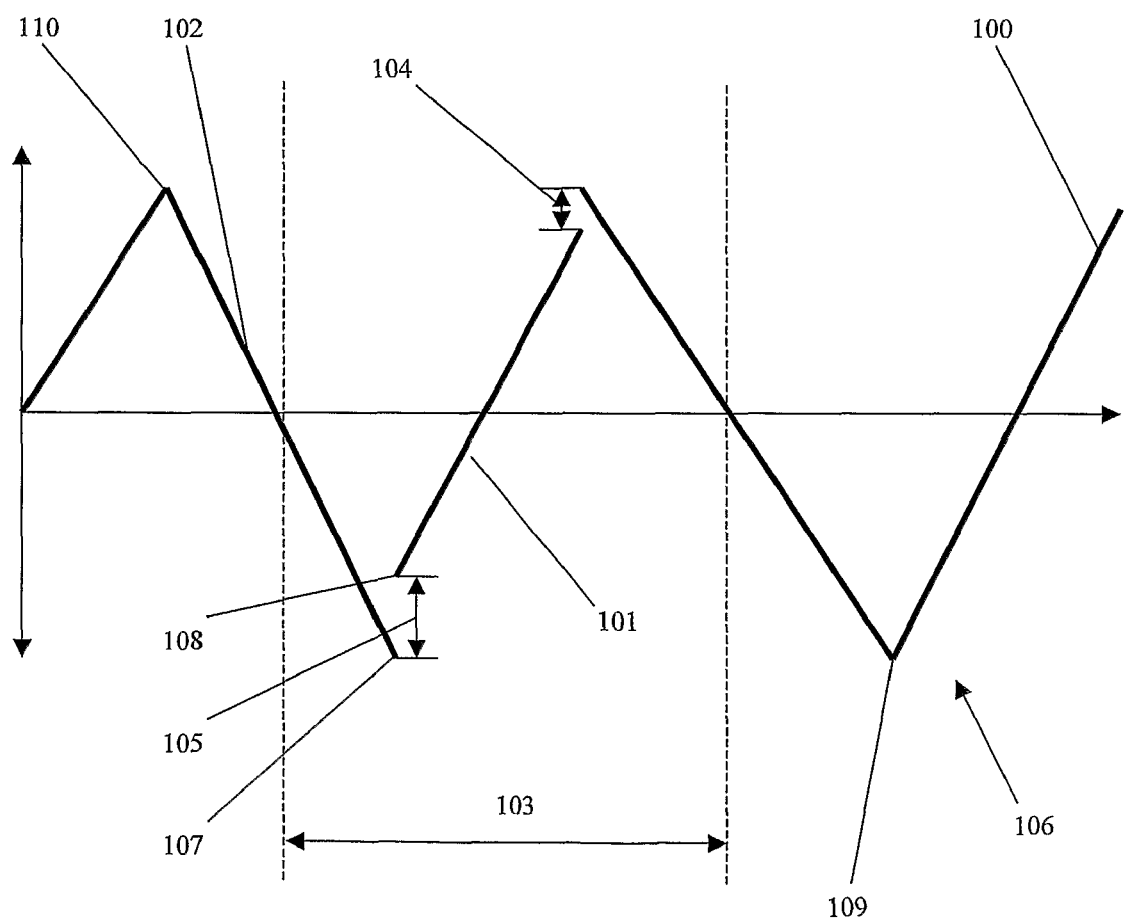
FIG. 4 and FIG. 5 depict graphs of back EMF voltages of a listening phase in the DC brushless motor of FIG. 1.
Figure 5:
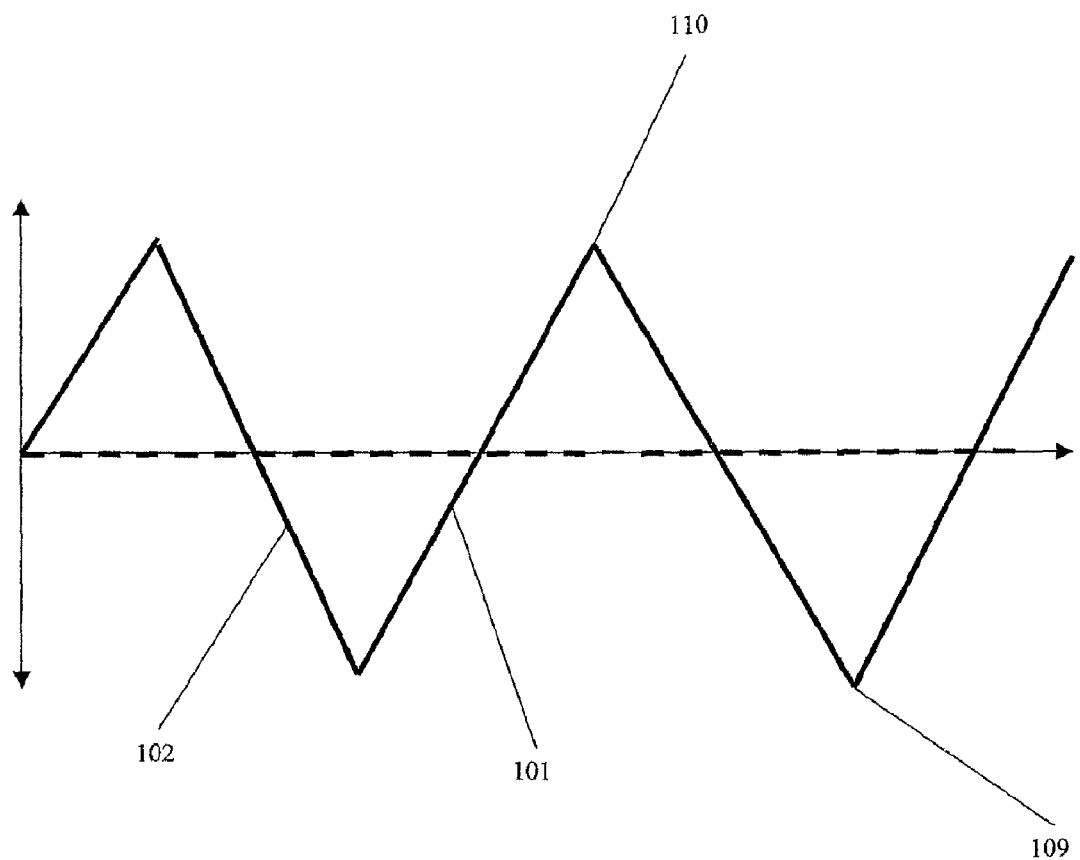

In order to have balanced rotational dynamics, the driving signals to the phases are constantly changed such that each phase is a driving phase or listening phase, depending on the particular switching cycle. Because of the particular configuration of the motor, for each switching cycle, the back EMF voltage generated in the particular listening phase varies between a minimal and maximum value or vice versa—between a maximum and minimum value. More details of this voltage dynamics are illustrated in FIGS. 3 to 5.

Figure 3:
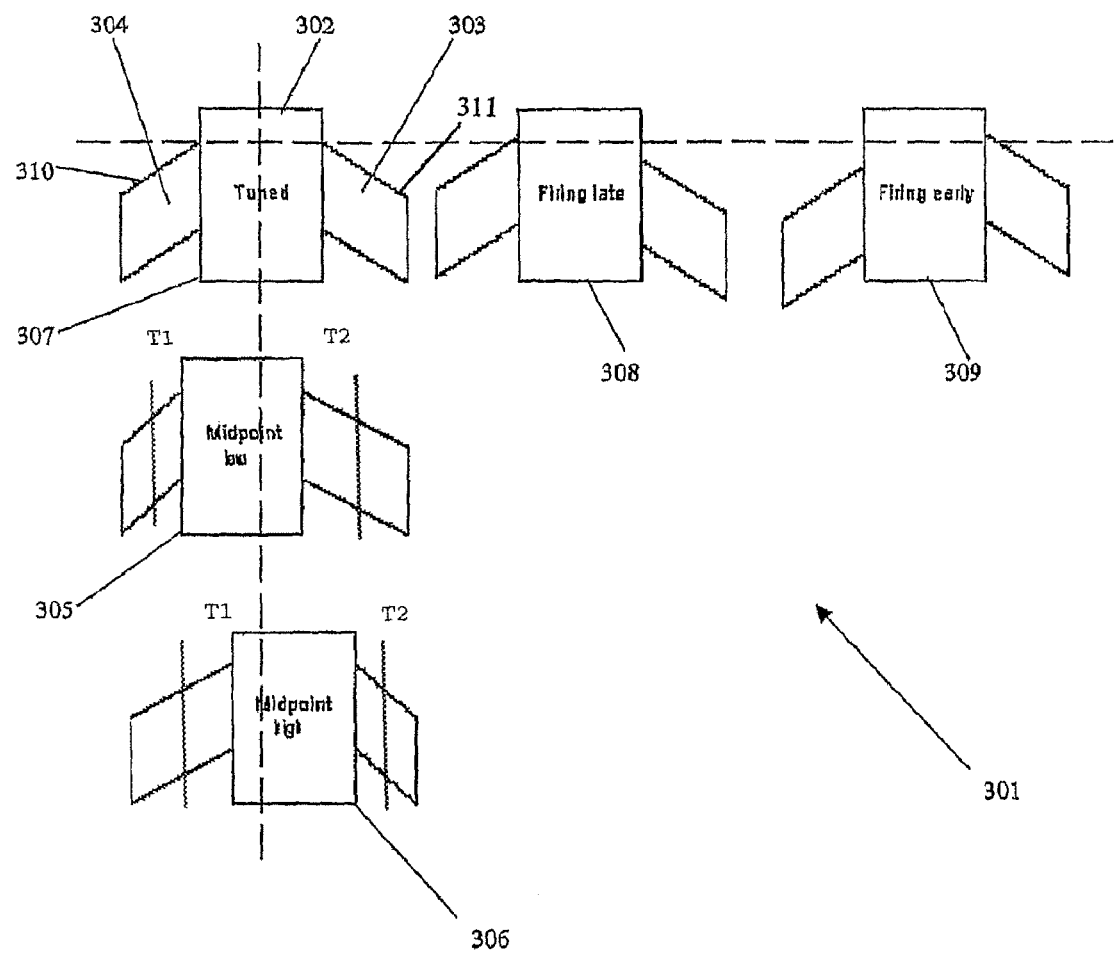
FIG. 3 depicts sample back EMF voltages of adjacent driving cycles of individual listening and energised phases in the DC brushless motor of FIG. 1.

The shape in the top left corner of FIG. 3 represents the voltage measured in a single phase during four driving cycles. Lines 310 and 311 illustrate the measured back EMF voltage during cycles where the phase is used as a listening phase. The ramping formations 304 and 303 to the left and right of the rectangular body 302 are defined by the fact that, even though the phase is not energized in these particular driving cycles, some interference from the DC driving signals sent to the other two phases is still detected. The driving signal is usually a train of square shaped pulses, usually oscillating between 0 and 12V. The duration of the pulses is modulated (PWM) to tune the motor excitation for varying torque requirements. The bottom line of the ramping formations 303 and 304 are defined by the "off" cycle, while the top lines 310 and 311 are defined by the "on" step of the driving signals such that the "thickness" of the ramp formation represents the amplitude of the interference by the driving signals in the other phases. At the same time, the slope of the ramp formation, illustrated by lines 310 and 311, represents the back EMF voltage change from a minimum to a maximum, which reflects the polarity change as a result of the rotor north to south or south to north transition, the midpoint being the zero crossing point. The vertical lines T1 and T2 in FIG. 3 show the locations of the midpoint relative to the start and end, respectively, of the switching cycle (represented by the rectangular blocks). The "on" step of the driving signal, defined by line 310, is obviously better defined and always available, while the "off" line defined by the bottom line of the ramping formation is not defined if the PWM is 100%, when there is not "off" step and the ramp formation is substituted by the single line 310. Thus, our future calculations and references for extreme values will refer to the minima and maxima of line 310. However it will be clear to a person skilled in the art that similar considerations and calculations would be applicable to the "off" line and using this line will be still within the scope of this invention.

The main rectangular body 302 illustrates two consecutive switching cycles where the specific phase receives driving signals. As mentioned above, the rectangular shape 302 represents the driving train of square shaped signals, varying between 0 and 12 volts. Finally, the right ramping formation 303 in FIG. 3 represents a further listening cycle of this specific phase. Because of the particular position of this phase with respect to the rotated magnetic configuration, now the generated back EMF voltage moves in the opposite direction, from maximum to a minimum value. Again, the generated back EMF voltage is superimposed to an interference of the driving signal in the other two phases and instead of a single line, the rhomboidal shape 303 of the ramp formation is observed.

The rising upper edge 310 of the left ramp formation and the falling upper edge 311 of the right ramp formation are used by the preferred embodiment of this invention for tuning of the DC brushless motor. Whereas in the illustrated case these two ramp formations represent the back EMF voltage measured by back EMF detector 7 during two adjacent listening cycles of a given phase, this can also be done for non-adjacent cycles. The adjustment is done in several stages.

First, the back EMF calculator 9 in FIG. 1 processes the signal of a single listening cycle and calculates midpoint voltage value between the minimum and maximum value in the increasing or decreasing back EMF voltage signal. In addition, the time delay for the back EMF voltage to change from the calculated midpoint value to the final minimum or maximum value is also calculated. The calculated midpoint EMF voltage value defines a reference voltage value, while the calculated time delay for the back EMF to reach the final extreme value defines a reference delay time. These values are then used during the next switching cycle. Detector 7 is used to monitor the back EMF voltage from the new listening phase in order to establish when this voltage will reach the reference voltage point. The system is configured such that speed controller 1 instructs pulse width modulator 2 and commutator 3 to provide driving signals to the corresponding driving phases with a time delay with respect to the reference voltage point, which time delay is equal to the reference delay time calculated for the previous cycle.

In perfect conditions, where there is no change in the working environment in the pump, the measured back EMF voltage from the various listening cycles of a phase would vary from minimum to maximum and from maximum to minimum values, wherein the minimum and maximum values for each listening cycle would be approximately the same. This is illustrated with shape 304 in FIG. 3, which represents a tuned DC brushless motor system. It can be seen that the upper edges 304 and 303 have a corresponding equal maxima and minima, the figure is symmetrical and the left and right ramp formations define the same slope with the rectangular shape in the middle.

However, as mentioned earlier, the real operating environment of a blood pump can change rapidly for various reasons. Accordingly, the timing of the driving signals to the corresponding phases will need to be changed. The system of the preferred embodiment performs, either simultaneously or consecutively, two adjustment routines.

One of them is illustrated in shape 308 in FIG. 3 wherein the later back EMF voltage signal of the later listening cycle of the phase (the right ramp formation of the shape), has minimum and maximum values which are smaller than the minimum and maximum values of the back EMF voltage signal of the earlier listening cycle of the phase (the left ramp formation of the shape). This is an indication that the driving voltage signals have been sent to the driving phases too late. Accordingly, the speed controller produces an instruction to the commutator to speed up the driving signals with a predetermined amount of time. This time can vary, depending of the particular application and is not essential to the performing of the invention. This is an iterative process and further measurements and adjustments are performed until the corresponding maximum and minimum values of the measured back EMF for two adjacent listening cycles become approximately equal.

The opposite situation is illustrated in shape 309 of FIG. 3, where the back EMF maximum and minimum values measured in a later listening cycle are higher than the corresponding values in the earlier listening cycle. This would indicate that driving signals are sent to the corresponding driving phases too early. Accordingly, the speed controller 1 would issue an instruction to the commutator to delay the firing signals with a predetermined amount of time. Again iterative measurements and adjustments are performed until the system is tuned.

A simplified graph, representing only a sequence of the upper edges of the back EMF voltage measured for a series of adjacent listening phases, is represented in FIG. 4. For simplicity, the intermediate driving cycles have been omitted. The offset 105 between the back EMF troughs 107 and 108, measured during the corresponding listening cycles 102 and 101, indicates that the driving signals have been fired too late. On the other hand, offset 104 between the corresponding peaks indicates that the driving signals have been fired too early and that a delay needs to be introduced.

A different situation is illustrated with shape 305 in FIG. 3. In this case, whereas the maximum and the minimum values for two adjacent listening cycles are approximately equal, the slopes of the back EMF voltage in the two adjacent listening phases (the left and the right ramp formation in shape 305) are different. In the particular case illustrated in shape 305, the second listening cycle has a smaller slope than the first listening cycle. This indicates that the midpoint of the back EMF is delayed (T2>T1), which has been assumed as a voltage reference level, is too low. Accordingly, the reference value for the back EMF voltage for the following switching cycle is increased by a predetermined step.

On the other hand, the configuration in shape 306, wherein the back EMF voltage slope of the second listening cycle is higher than that of the first listening cycle, indicates that the reference back EMF voltage midpoint is too high, or the back EMF is early (T2<T1). If such configuration is observed, the speed controller 1 issues an instruction for decreasing the reference midpoint voltage with a predetermined step. As in the previous case, these adjustments are iterative and are performed until a well-balanced symmetrical figure such as that in the top left corner of FIG. 3 is achieved. The simplified, listening phase only graph for the measured back EMF signal of a well tuned system is illustrated in FIG. 5. This graph clearly shows how the back EMF voltages of adjacent listening phases of a well tuned system have equal extreme values 109, 110 and slopes 101, 102.

The adjustments of the timing of the driving signal and the back EMF midpoint reference level effectively relate to timing of the driving signals. Thus, even though they are still two separate adjustments and can be performed separately from each other, it is highly recommended that these two adjustments be performed together in a combined iterative routine. Such a calculation and adjustment can be performed each driving cycle or only every number of cycles.

It is envisaged that the above-described routine is preferably performed with the top edges 310 and 303 of the left and right ramp formations in FIG. 3 and, accordingly, the back EMF voltages used in the calculations will be all positive. However, if the lower edge of shape 304 is used, it may be preferable to use as a midpoint the zero crossing point of the back EMF voltage.

It will be clear to a skilled addressee that the system and the method according to this invention offer a useful method for dynamically and continuously tuning a DC brushless motor in response to the changes in the working environment of the motor.

While the preferred embodiment is described in the context of an implantable blood pump, it is understood that the system and the method of the preferred embodiment are applicable to any fluid pump and, indeed, to any DC brushless motor, where change in the surrounding environment have to be taken into account by introducing appropriate tuning into the working regime of the motor. One example is the varying load imposed on the agitator of a washing machine, where the drive mechanism includes a DC brushless motor.

The above description details only some of the embodiments of the present invention. Modifications may be obvious to those skilled in the art and may be made without departing from the scope and spirit of the present invention.

The terms "comprising" and "including" and their grammatical variations, as used herein, are used in an inclusive sense and not in the exclusive sense of "consisting of".

The invention claimed is:

1. A method of tuning a DC brushless motor having a rotor and a stator, the stator having at least three phases,
the method including the steps of:
during a first cycle of the motor, detecting the back EMF voltage from a first listening phase and calculating a first time delay from the detected back EMF voltage;
during a second cycle of the motor, detecting the back EMF voltage from a second listening phase and calculating a second time delay from the detected back EMF voltage;
comparing the first and second time delays and if they are different, providing an amended time delay; and
providing a driving signal including the amended time delay to the driving phases of the stator to compensate for the difference in the first and second time delays.

2. The method as claimed in claim 1, wherein the motor is included in a fluid pump and the tuning is in response to variations in the fluid characteristics and/or fluid dynamics characteristics of the pumped fluid.

3. The method as claimed in claim 2, wherein the fluid pump is included in an implantable medical device, and the fluid is blood.

4. The method as claimed in claim 1, further including:
comparing extreme values for both cycles and, if there is a difference between the corresponding extreme values, determining the amended delay time to account for the difference; and
comparing the rate of change of the back EMF voltage for each cycle and, if different, amending a reference voltage value and applying a time delay with respect to the amended reference voltage value.

5. A method of tuning a DC brushless motor, wherein measurement of back EMF voltage is used to detect changes in the torque requirements caused by variation in the operating conditions of the DC brushless motor, the method including varying the timing of the driving signals to the motor to compensate for the changes in the torque requirements, wherein the motor comprises a rotor and a stator, the stator including at least three phases, wherein alternating driving signals are provided simultaneously to at least two of the at least three phases such that each switching cycle is a driving cycle for at least two phases that receive driving signals during this cycle, and the same switching cycle is also a listening cycle for at least one phase that is non-energized during this cycle, the motor being arranged such that, for a given switching cycle, a rotation of the rotor generates in the at least one listening phase a back EMF voltage that varies between two extreme values, the method including the steps of:
for at least one reference switching cycle:
detecting the back EMF voltage from the at least one listening phase;
determining the back EMF voltage corresponding to the midpoint value between the extreme values to define a reference voltage value; and
calculating the time delay for the back EMF voltage to change from the midpoint value to the final extreme value to define a reference delay time;
then, for at least one further switching cycle having a further at least one listening phase and a further set of at least two driving phases, the further cycle being subsequent to the reference cycle:
monitoring the back EMF voltage in the further listening phase and, when the EMF voltage reaches a value equal to the reference voltage value of the reference switching cycle, providing a driving signal to the corresponding driving phases with a time delay with respect to the reference voltage point, which time delay is equal to the reference delay time.

6. The method as claimed in claim 5, the method further including comparing the back EMF voltage for two listening cycles of at least one phase and performing at least one of the following steps:
comparing the extreme values for both cycles and, if there is a difference between the corresponding extreme values, amending the reference delay time; and comparing the rate of change of the back EMF voltage and, if different, amending the reference voltage value with respect to the previously determined midpoint value.

7. The method as claimed in claim 6, wherein amending the reference delay time comprises:
   if the extreme back EMF voltage values of the later cycle are smaller than the corresponding values of the earlier cycle, reducing the reference delay time for the following driving cycle; and
   if the extreme back EMF voltage values of the later cycle are bigger than the corresponding values of the earlier cycle, increasing the reference delay time for the following driving cycle.

8. The method as claimed in claim 6, wherein amending the reference voltage values comprises:
   if the rate of change of the back EMF voltage of the later cycle is smaller than the rate of change of the back EMF voltage for the earlier cycle, increasing the reference voltage value for the following driving cycle; and
   if the rate of change of the back EMF voltage of the later cycle is larger than the rate of change of the back EMF voltage for the earlier cycle, reducing the reference voltage value for the following driving cycle.

9. The DC brushless motor system as claimed in claim 6, wherein the midpoint is a zero-crossing.

10. The method as claimed in claim 5, wherein the switching cycle is adjacent to the reference cycle and/or the two compared listening cycles are adjacent.

11. The method as claimed in claim 5, wherein the tuning is effected either each switching cycle or each number of switching cycles.

12. The DC brushless motor system as claimed in claim 5, wherein the midpoint is a zero-crossing.

13. A DC brushless motor system with varying characteristics of the input drive signals, comprising:
   a rotor and a stator having at least three phases;
   a sensor for detecting the back EMF voltage from a listening phase of at least one of the three phases;
   a back EMF calculator associated with the sensor and arranged for determining,
      during a first switching cycle, a first voltage value and delay time equal to the delay time for the back EMF voltage to change from the first voltage value to a final extreme value for the first switching cycle,
      during a second, subsequent switching cycle, a second voltage value and delay time equal to the delay time for the back EMF voltage to change from the second voltage value to a final extreme value for the second switching cycle, and
      comparing the first and second delay times and if they are different, determining an amended delay time to account for the difference; and
   a speed controller configured to provide during a cycle subsequent to the second cycle the amended delay time with a driving signal corresponding to driving phases of the stator.

14. The DC brushless motor system as claimed in claim 13, wherein the back EMF calculator is further configured to compare the back EMF voltage for the first and second switching cycles and perform at least one of the following steps:
   comparing the extreme values for both cycles and, if there is a difference between the corresponding extreme values, determining the amended delay time to account for the difference; and
   comparing the rate of change of the back EMF voltage and, if different, amending a reference voltage value and applying a time delay with respect to the amended reference voltage value.

15. The DC brushless motor system as claimed in claim 13, the system being arranged for inclusion in a fluid pump, the tuning being required in response to variations in the fluid characteristics and/or fluid dynamics characteristics of the pumped fluid.

16. The system as claimed in claim 15, wherein the fluid pump is included in an implantable medical device, and the fluid is blood.

17. A DC brushless motor system with varying characteristics of the input drive signals, wherein measurement of back EMF voltage is used to detect changes in the torque requirements caused by variation in the operating conditions of the motor, the system being configured to vary the timing of the driving signals to the motor to compensate for the changes in the torque requirements, the motor system comprising a rotor and a stator, the stator including at least three phases, wherein alternating driving signals are provided simultaneously to at least two of the at least three phases such that each switching cycle is a driving cycle for at least two phases that receive driving signals during this switching cycle and is a listening cycle for at least one listening phase that is non-energized during this cycle, the motor system being arranged such that, for a given switching cycle, a rotation of the rotor generates in the at least one listening phase a back EMF voltage that varies between two extreme values, the system further comprising:
   a sensor for detecting the back EMF voltage from the listening phase;
   processing means associated with the sensor and arranged for determining, during a reference switching cycle, a reference voltage value equal to the midpoint voltage value between the two corresponding extreme values and calculating a reference delay time equal to the delay time for the back EMF voltage to change from the midpoint value to the final extreme value; and
   control means for providing, during at least one cycle that is further to the reference cycle, a driving signal to the corresponding driving phases with a delay, with respect to the reference voltage value, which is equal to the determined reference delay time.

18. The DC brushless motor system as claimed in claim 17, wherein the processing means are further configured to compare the back EMF voltage for two listening cycles of at least one phase and perform at least one of the following steps:
   comparing the extreme values for both cycles and, if there is a difference between the corresponding extreme values, amending the reference delay time; and
   comparing the rate of change of the back EMF and, if the rate of change of the back EMF is different, amending the voltage reference value with respect to the previously determined midpoint value and applying a time delay with respect to the amended reference voltage value.

19. The DC brushless motor system as claimed in claim 18, wherein amending the reference delay time comprises:
   if the extreme back EMF voltage values of the later cycle are smaller than the corresponding values of the earlier cycle, reducing the reference delay time for the following driving cycle; and
   if the extreme back EMF voltage values of the later cycle are bigger than the corresponding values of the earlier cycle, increasing the reference delay time for the following driving cycle.

20. The DC brushless motor system as claimed in claim 19, wherein amending the reference delay time further comprises
if the midpoint occurs earlier then the reference midpoint, decrease the PWM on duration of the driving train, and
if the midpoint occurs later then the reference midpoint, increase the PWM on duration of the driving train.

21. The DC brushless motor system as claimed in claim 20, wherein the midpoint is a zero-crossing.

22. The DC brushless motor system as claimed in claim 18, wherein amending the reference voltage values comprises:
if the rate of change of the back EMF voltage of the later cycle is smaller than the rate of change of the back EMF voltage for the earlier cycle, increasing the reference voltage value for the following driving cycle; and
if the rate of change of the back EMF voltage of the later cycle is larger than the rate of change of the back EMF voltage for the earlier cycle, reducing the reference voltage value for the following driving cycle.

23. The DC brushless motor system as claimed in claim 17, wherein the switching cycle is adjacent to the reference cycle and/or the two compared listening cycles are adjacent.

24. The DC brushless motor system as claimed in claim 17, wherein the tuning is effected either each switching cycle or each number of switching cycles.

25. The DC brushless motor system as claimed in claim 17, wherein the midpoint is a zero-crossing.

26. A method of tuning a DC brushless motor integrated in a blood pump, wherein measurement of back EMF voltage is used to detect changes in the torque requirements caused by variation in the blood characteristics or blood dynamics characteristics, the method including varying the timing of the drive signals to the motor to compensate for the changes in the torque requirements, wherein the motor comprises a rotor and a stator, the stator including at least three phases, wherein alternating driving signals are provided simultaneously to at least two of the at least three phases such that, each switching cycle is a driving cycle, for at least two of the phases that receive driving signals, and the same switching signal is a listening cycle for at least one listening phase that is non-energized during this cycle, the motor being arranged such that, for a given switching cycle, a rotation of the rotor generates in the at least one listening phase a back EMF voltage that varies between two extreme values, the method including the steps of:

for at least one reference switching cycle:
detecting the back EMF voltage from the at least one listening phase;
determining the back EMF voltage corresponding to the midpoint value between the extreme values to define a reference voltage value; and
calculating the time delay for the back EMF voltage to change from the midpoint value to the final extreme value to define a reference delay time;
then, for at least one further switching cycle having a further at least one listening phase and a further set of at least two driving phases, the further cycle being subsequent to the reference cycle,
monitoring the back EMF voltage in the further listening phase and, when the EMF voltage reaches a value equal to the reference voltage value providing a driving signal to the corresponding driving phases with a time delay with respect to the reference voltage point equal to the reference delay time.

27. The method as claimed in claim 26, the method further including comparing the back EMF voltage for two adjacent listening cycles of a single phase and performing at least one of the following steps:
comparing the extreme values for both cycles and,
if the extreme back EMF voltage values of the later cycle are smaller than the corresponding values of the earlier cycle, reducing the reference delay time for the following driving cycle; and
if the extreme back EMF voltage values of the later cycle are bigger than the corresponding values of the earlier cycle, increasing the reference delay time for the following driving cycle; and
comparing the rate of change of the back EMF voltage and,
if the rate of change of the back EMF voltage of the later cycle is smaller than the slope of the back EMF voltage for the earlier cycle, increasing the reference voltage value for the following driving cycle; and
if the rate of change of the back EMF voltage of the later cycle is larger than the rate of change of the back EMF voltage for the earlier cycle, reducing the reference voltage value for the following driving cycle.

28. The DC brushless motor system as claimed in claim 26, wherein the midpoint is a zero-crossing.

* * * * *